United States Patent
Tang et al.

(10) Patent No.: US 11,650,201 B2
(45) Date of Patent: May 16, 2023

(54) ANASTASIS BIOSENSOR

(71) Applicant: THE JOHNS HOPKINS UNIVERSITY, Baltimore, MD (US)

(72) Inventors: Ho Lam Tang, Baltimore, MD (US); Ho Man Holly Tang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 756 days.

(21) Appl. No.: 16/461,398

(22) PCT Filed: Nov. 16, 2017

(86) PCT No.: PCT/US2017/061973
§ 371 (c)(1),
(2) Date: May 16, 2019

(87) PCT Pub. No.: WO2018/094020
PCT Pub. Date: May 24, 2018

(65) Prior Publication Data
US 2021/0278394 A1    Sep. 9, 2021

Related U.S. Application Data

(60) Provisional application No. 62/422,689, filed on Nov. 16, 2016.

(51) Int. Cl.
*C12N 9/96* (2006.01)
*G01N 33/50* (2006.01)

(52) U.S. Cl.
CPC ........... *G01N 33/5005* (2013.01); *C12N 9/96* (2013.01); *C07K 2319/03* (2013.01); *C07K 2319/50* (2013.01); *C07K 2319/60* (2013.01); *G01N 2510/00* (2013.01)

(58) Field of Classification Search
CPC ............ C07K 2319/00; C07K 2319/03; C07K 2319/50; C07K 2319/60; C07K 14/00; C12N 9/96; C12Q 1/34
See application file for complete search history.

(56) References Cited

U.S. PATENT DOCUMENTS

| | | | |
|---|---|---|---|
| 7,354,735 | B2 | 4/2008 | Chang et al. |
| 2007/0231865 | A1 | 10/2007 | Spears et al. |
| 2009/0131270 | A1 | 5/2009 | Taylor et al. |

FOREIGN PATENT DOCUMENTS

| | | | |
|---|---|---|---|
| RU | 2493260 C2 * | 9/2013 | |
| RU | 2493260 C2 | 9/2013 | |
| WO | 1999025840 A1 | 5/1999 | |
| WO | 2000073802 A1 | 7/2000 | |
| WO | 2000/073802 A1 | 12/2000 | |
| WO | 2001/075453 A2 | 10/2001 | |
| WO | 2006/017751 A2 | 2/2006 | |
| WO | 2013/134499 A1 | 9/2013 | |

OTHER PUBLICATIONS

Aitken, et al., Apoptosis in the germ line. Reproduction 141, 139-150. (2011).
Arama, et al., Caspase activity and a specific cytochrome Care required for sperm differentiation in *Drosophila*. Dev Cell 4, 687-697. (2003).
Bloom, Induced chromosomal aberrations: biological and clinical significance. J Pediatr 81, 1-8. (1972).
Boffetta, et al., Alcohol and cancer. Lancet Oncol 7, 149-156. (2006).
Capy, et al., Stress and transposable elements: co-evolution or useful parasites? Heredity 85, 101-106. (2000).
Chabaud, et al., Apoptosis modulation as a promising target for treatment of systemic sclerosis. Int J Rheumatol 2011, 495792. (2011).
Chipuk, et al., The BCL-2 family reunion. Mol Cell 37, 299-310. (2010).
Cifone, et al., Correlation of patterns of anchorage-independent growth with in vivo behavior of cells from a murine fibrosarcoma. Proc Natl Acad Sci USA 77, 1039-1043. (1980).
Coleman, et al., Membrane blebbing during apoptosis results from caspase-mediated activation of ROCK I. Nat Cell Biol 3, 339-345. (2001).
Drummond-Barbosa, et al., Stem cells and their progeny respond to nutritional changes during *Drosophila oogenesis*. Dev Biol 231, 265-278. (2001).
Enari, et al., A caspase-activated DNase that degrades DNA during apoptosis, and its inhibitor ICAD. Nature 391, 43-50. (1998).
Fenech, Cytokinesis-block micronucleus cytome assay. Nat Protoc 2, 1084-1104. (2007).
Fischer, et al., Apoptosis-based therapies and drug targets. Cell Death Differ 12 (Suppl 1), 942-961. (2005).
Fu, et al., Balancing repair and tolerance of DNA damage caused by alkylating agents. Nat Rev Cancer 12, 104-120. (2012).

(Continued)

*Primary Examiner* — Karen Cochrane Carlson
(74) *Attorney, Agent, or Firm* — Johns Hopkins Technology Ventures

(57) ABSTRACT

The present invention relates to the field of anastasis, i.e., the process of reversal of apoptosis. More specifically, the present invention provides methods and compositions useful for studying anastasis. The present invention also provides a biosensor comprising (a) a split transcription factor complex comprising one half of a split transcription factor linked to a transmembrane domain via an enzyme cleavable linker; (b) a split transcription factor comprising the other half of the split transcription factor linked to a MTS via an enzyme-cleavable linker; and (c) a reporter system comprising (1) a first nucleic acid encoding a site specific recombinase operably linked to the site specific sequence for the transcription factor; and (2) a second nucleic acid comprising a stop codon cassette flanked by site specific recombination sequences, wherein the split transcription factor is Gal 4 or split Q. In other embodiments, the recombinase is Cre or FLP.

25 Claims, 2 Drawing Sheets
Specification includes a Sequence Listing.

(56) References Cited

OTHER PUBLICATIONS

Fuchs, et al., Programmed cell death in animal development and disease. Cell 147, 742-758. (2011).
German, Cytological evidence for crossing-over in vitro in human lymphoid cells. Science 144, 298-301. (1964).
Goldin, et al., Apoptotic bodies in a murine model of alcoholic liver disease: reversibility of ethanol-induced changes. J Pathol 171, 73-76. (1993).
Gordon, et al., Causes and consequences of aneuploidy in cancer. Nat Rev Genet 13, 189-203. (2012).
Gordon, et al., DNA damage and repair in light-induced photoreceptor degeneration. Invest Ophthalmol Visual Sci 43, 3511-3521. (2002).
Green, et al., The pathophysiology of mitochondrial cell death. Science 305, 626-629. (2004).
Guicciardi, et al., Apoptosis as a mechanism for liver disease progression. Semin Liver Dis 30, 402-410. (2010).
Hu, et al., Molecular cloning and expression of a functional anti-inflammatory protein, Sj16, of Schistosoma japonicum. Int J Parasitol 39, 191-200. (2009).
Iravanian, et al., Functional reentry in cultured monolayers of neonatal rat cardiac cells. Am J Physiol Heart Circ Physiol 285, H449-H456. (2003).
Jacobson, et al., Programmed cell death in animal development. Cell 88, 347-354. (1997).
Jaiswal, et al., Long-term multiple color imaging of live cells using Quantum Dot bioconjugates. Nat Biotechnol 21, 47-51. (2003).
Jiang, et al., An active DNA transposon family in rice. Nature 421, 163-167. (2003).
Johnstone, et al., Apoptosis: a link between cancer genetics and chemotherapy. Cell 108, 153-164. (2002).
Kerr, et al., Apoptosis: a basic biological phenomenon with wide-ranging implications in tissue kinetics. Br J Cancer 26, 239-257. (1972).
Kroemer, et al., Classification of cell death: recommendations of the Nomenclature Committee on Cell Death 2009. Cell Death Differ 16, 3-11. (2009).
Lazebnik, et al., Cleavage of poly(ADP-ribose) polymerase by a proteinase with properties like ICE. Nature 371, 346-347. (1994).
Li, et al., Endo nuclease G is an apoptotic DNase when released from mitochondria. Nature 412, 95-99. (2001).
Liu, et al., Chromosome catastrophes involve replication mechanisms generating complex genomic rearrangements. Cell 146, 889-903. (2011).
Liu, et al., DFF, a heterodimeric protein that functions downstream of caspase-3 to trigger DNA fragmentation during apoptosis. Cell 89, 175-184 (1997).
Logue, et al., Expression, purification and use of recombinant annexin V for the detection of apoptotic cells. Nat Protoc 4, 1383-1395. (2009).
Luthi, et al., The CASBAH: a searchable database of caspase substrates. Cell Death Differ 14, 641-650. (2007).
MacLeod, et al., Cytogenetic harvesting of commonly used tumor cell lines. Nat Protoc 2, 372-3 82. (2007).
Masters, HeLa cells 50 years on: the good, the bad and the ugly. Nat Rev Cancer2, 315-319. (2002).
McClintock, The significance of responses of the genome to challenge. Science 226, 792-801. (1984).
McKechnie, et al., Recovery of the rabbit retina after light damage (preliminary observations). Albrecht Von Graefes Arch Klin Exp Ophthalmol 212,271-283. (1980).
McKillop, et al., Alcohol and liver cancer. Alcohol 35, 195-203. (2005).
Milligan, et al., Thephosphatidylinositol transfer protein domain of Drosophila retinal degeneration B protein is essential for photoreceptor cell survival and recovery from light stimulation. J Cell Biol 139,351-363. (1997).
Narula, et al., Mechanisms ofdisease: apoptosis in heart failure-seeing hope in death. Nat Clin Pract Cardiovasc Med 3,681-688. (2006).
Narula, et al., Apoptosis in heart failure: release of cytochrome c frommitochondria and activation of caspase-3 in human cardiomyopathy. Proc Natl Acad Sci USA 96, 8144-8149. (1999).
Olive, et al., The comet assay: a method to measure DNA damage in individual cells. Nat Protoc 1, 23-29.(2006).
Reed, et al., Postmitochondrial regulation of apoptosisduring heart failure. Proc Natl Acad Sci USA 96, 7614-7616. (1999).
Riedl, et al., Molecular mechanisms of caspase regulation duringapoptosis. Nat Rev Mol Cell Biol 5, 897-907. (2004).
Rosenberg, Evolving responsively: adaptive mutation. Nat Rev Genet 2, 504-515. (2001).
Ross, Induction of cell death by radiotherapy. Endocr Related Cancer 6, 41-44. (1999).
Rubin, Cell-cell contact interactions conditionally determine suppression and selection of the neoplastic phenotype. Proc Natl Acad Sci USA 205, 6215-6221. (2008).
Salinas, et al., Stress-induced gem1 cellapoptosis is by a p53 independent pathway in Caenorhabditis elegans. Cell Death Differ 13,2 129-2139. (2006).
Office Action dated Feb. 10, 2017 in related U.S. Appl. No. 14/383,156.
Response to Office Action dated Feb. 10, 2017 in related U.S. Appl. No. 14/383,156.
Final Office Action dated Oct. 12, 2018 in related U.S. Appl. No. 14/383,156.
Office Action dated Jun. 22, 2016 in related U.S. Appl. No. 14/383,156.
Response to Final Office Action dated Jun. 22, 2016 in related U.S. Appl. No. 14/383,156.
Office Action dated Jan. 30, 2018 in related U.S. Appl. No. 14/383,156.
Response to Office Action dated Jan. 30, 2018 in related U.S. Appl. No. 14/383,156.
Albeck, J., et al., "Quantitative analysis of pathways controlling extrinsic apoptosis in single cells" Molecular Cell 30, pp. 11-25, Apr. 11, 2008.
Extended European Search Report dated May 18, 2020 for related EPO application 17870867.3.
Sawicki, et al., On the recovery of transcription after inhibition by actinomycin D. J Cell Biol 55, 299-309. (1972).
Stephens, et al., Massive genomic rearrangement acquired in a single catastrophic event during cancer development. Cell 144, 27-40. (2011).
Stratton, et al., The cancer genome. Nature 458, 719-724. (2009).
Susin, et al., Molecular characterization of mitochondrial apoptosis-inducing factor. Nature 397, 441-446. (1999).
Takemoto, et al., Spatio-temporal activation of caspase revealed by indicator that is insensitive to environmental effects. J Cell Biol 160, 235-243. (2003).
Talanian, et al., Substrate specificities of caspase family proteases. J Biol Chem 272, 9677-9682. (1997).
Tang, et al., Reversibility of apoptosis in cancer cells. Br J Cancer 100, 118-122. (2009).
Taylor, et al., Apoptosis: controlled demolition at the cellular level. Nat Rev Mol Cell Biol 9, 231-241. (2008).
Wang, et al., PARP is important for genomic stability but dispensable in apoptosis. Genes Dev 11, 2347-2358. (1997).
Zurlo, et al., Characterization of a primary hepatocyte culture system for toxicological studies. In Vitro Cell Dev Biol Anim 32, 211-220. (1996).
Evans, et al., G-TRACE: rapid Gal4-based cell lineage analysis in Drosophila. Nat Methods 6, 603-605. (2009).
Bardet, et al., A fluorescent reporter of caspase activity for live imaging. Proc Natl Acad Sci U S A 105, 13901-5 (2008).
Ditzel, et al., Degradation of DIAP1 by the N-end rule pathway is essential for regulating apoptosis. Nat Cell Biol 5, 467-473. (2003).
Badea, et al., A noninvasive genetic/pharmacologic strategy for visualizing cell morphology and clonal relationships in the mouse. J Neurosci 15, 2313-2322 (2003).

(56) References Cited

OTHER PUBLICATIONS

Steiner, et al., An in vivo assay for the identification of target proteases which cleave membrane-associated substrates. FEBS Lett 17, 245-249. (1999).
Tang, et al., Cell survival, DNA damage, and oncogenic transformation following a transient and reversible apoptotic response. Mol Biol Cell 23, 2240-2251. (2012).
Goyal, et al., Induction of apoptosis by Drosophila reaper, hid and grim through inhibition of IAP function. EMBO J 19, 589-97 (2000).
Garg, et al., Apoptosis and heart failure: clinical relevance and therapeutic target. JMol Cell Cardiol 38, 73-9 (2005).
Venkatachalam, et al., Motor deficit in a Drosophila model of mucolipidosis type IV due to defective clearance of apoptotic cells. Cell 135, 838-51 (2008).
Yi, et al., Rapid cold-hardening protects Drosophila melanogaster from cold-induced apoptosis. Apoptosis 12, 1183-93 (2007).
Ranganathan, Matter of Life or Death. Science 299, 1677-1679 (2003).
Li, et al., Selective anticancer strategies via intervention of the death pathways relevant to cell transformation. Cell Death Differ 15, 1197-210 (2008).
Abbott, Ultrastructure of cell death in gamma- or X-irradiated imaginal wing discs of Drosophila. Radiat Res 96, 611-27 (1983).
Pritchett, et al., Cracking open cell death in the Drosophila ovary. Apoptosis 14, 969-79 (2009).
Kitamoto, Conditional modification of behavior in Drosophila by targeted expression of a temperature-sensitive shibire allele in defined neurons. JNeurobiol 47, 81-92 (2001).
Silva, et al., ATM is required for telomere maintenance and chromosome stability during Drosophila development. Curr Biol 14, 1341-7 (2004).
Mollereau, et al., Photoreceptor differentiation in Drosophila: from immature neurons to functional photoreceptors. Dev Dyn 232, 585-92 (2005).
Gambis, et al., Two-color in vivo imaging of photoreceptor apoptosis and development in Drosophila. Dev Biol 351, 128-34 (2011).
Pichaud, et al., A new visualization approach for identifying mutations that affect differentiation and organization of the Drosophila ommatidia. Development 128, 815-26 (2001).
Geisbrecht, et al., A role for Drosophila IAP1-mediated caspase inhibition in Racdependent cell migration. Cell 118, 111-25 (2004).
Helfer, et al., Caspase-8 promotes cell motility and calpain activity under nonapoptotic conditions. Cancer Res 66, 4273-8 (2006).
Malhi, et al., Hepatocyte death: a clear and present danger. Physiol Rev 90, 1165-94 (2010).
Lin, et al., Mitochondrial dysfunction and oxidative stress in neurodegenerative diseases. Nature 443, 787-95 (2006).
Yang, et al., Excessive Dpp signaling induces cardial apoptosis through dTAKI and dJNK during late embryogenesis of Drosophila. JBiomed Sci 18, 85 (2011).
Tain, et al., Drosophila HtrA2 is dispensable for apoptosis but acts downstream of PINK 1 independently from Parkin. Cell Death Differ 16, 1118-25 (2009).
Stoller, et al., Ore reporter mouse expressing a nuclear localized fusion of GFP and betagalactosidase reveals new derivatives of Pax3-expressing precursors. Genesis 46, 200-4 (2008).
Cordeiro, et al., Imaging multiple phases of neurodegeneration: a novel approach to assessing cell death in vivo. Cell Death Dis 1, e3 (2010).
Youssef, et al., Retinal light toxicity. Eye (Loud) 25, 1-14 (2011).
Saito, et al., Involvement of ceramide in ethanol-induced apoptotic neurodegeneration in the neonatal mouse brain. JNeurochem 115, 168-77 (2010).
Waldmeier, et al., Interrupting apoptosis in neurodegenerative disease: potential for effective therapy? Drug Discov Today 9, 210-218. (2004).

\* cited by examiner

SEQUENCE LISTING

<160> NUMBER OF SEQ ID NOS: 7

<210> SEQ ID NO 1
<211> LENGTH: 4
<212> TYPE: PRT

```
<213> ORGANISM: Artificial Sequence
<220> FEATURE:
<223> OTHER INFORMATION: enzyme cleavable linker

<400> SEQUENCE: 1

Asp Glu Val Asp
1

<210> SEQ ID NO 2
<211> LENGTH: 4
<212> TYPE: PRT
<213> ORGANISM: Artificial Sequence
<220> FEATURE:
<223> OTHER INFORMATION: enzyme cleavable linker

<400> SEQUENCE: 2

Cys Ala Val Pro
1

<210> SEQ ID NO 3
<211> LENGTH: 4
<212> TYPE: PRT
<213> ORGANISM: Artificial Sequence
<220> FEATURE:
<223> OTHER INFORMATION: peptide linker

<400> SEQUENCE: 3

Cys Ala Ala Ala
1

<210> SEQ ID NO 4
<211> LENGTH: 4
<212> TYPE: PRT
<213> ORGANISM: Artificial Sequence
<220> FEATURE:
<223> OTHER INFORMATION: peptide linker

<400> SEQUENCE: 4

Asp Glu Val Ala
1

<210> SEQ ID NO 5
<211> LENGTH: 12
<212> TYPE: PRT
<213> ORGANISM: Artificial Sequence
<220> FEATURE:
<223> OTHER INFORMATION: DEVD derived from PARP sequence

<400> SEQUENCE: 5

Lys Arg Lys Gly Asp Glu Val Asp Gly Val Asp Glu
1               5                   10

<210> SEQ ID NO 6
<211> LENGTH: 204
<212> TYPE: DNA
<213> ORGANISM: Artificial Sequence
<220> FEATURE:
<223> OTHER INFORMATION: Mito-CAVP (N-terminal end of SMAC)

<400> SEQUENCE: 6
atggcggctc tgaagagttg gctgtcgccc atcgtaactt cattcttcag gtacagacag      60
tgtttgtgtg ttcctgttgt ggctaacttt aagaagcggt gtttctcaga attgataaga     120
ccatggcaca aaactgtgac gattggcttt ggagtaaccc tgtgtgcggt tcctattgca     180
cagaaatcag agcctcattc cctt                                            204
```

```
<210> SEQ ID NO 7
<211> LENGTH: 68
<212> TYPE: PRT
<213> ORGANISM: Artificial Sequence
<220> FEATURE:
<223> OTHER INFORMATION: Mito-CAVP (N-terminal end of SMAC)

<400> SEQUENCE: 7

Met Ala Ala Leu Lys Ser Trp Leu Ser Arg Ser Val Thr Ser Phe Phe
1               5                   10                  15

Arg Tyr Arg Gln Cys Leu Cys Val Pro Val Val Ala Asn Phe Lys Lys
                20                  25                  30

Arg Cys Phe Ser Glu Leu Ile Arg Pro Trp His Lys Thr Val Thr Ile
            35                  40                  45

Gly Phe Gly Val Thr Leu Cys Ala Val Pro Ile Ala Gln Ala Val Tyr
        50                  55                  60

Thr Leu Thr Ser
65
```

ANASTASIS BIOSENSOR

CROSS-REFERENCE TO RELATED APPLICATIONS

This application is a 35 U.S.C. § 371 U.S. national entry of International Application PCT/US2017/061973, having an international filing date of Nov. 16, 2017, which claims the benefit of U.S. Provisional Application No. 62/422,689, filed Nov. 16, 2016, the content of each of the aforementioned applications is herein incorporated by reference in their entirety.

FIELD OF THE INVENTION

The present invention relates to the field of anastasis, i.e., the process of reversal of apoptosis. More specifically, the present invention provides methods and compositions useful for studying anastasis.

INCORPORATION-BY-REFERENCE OF MATERIAL SUBMITTED ELECTRONICALLY

This application contains a sequence listing. It has been submitted electronically via EFS-Web as an ASCII text file entitled "P14439-02_ST25.txt." The sequence listing is 2,204 bytes in size, and was created on Nov. 16, 2017. It is hereby incorporated by reference in its entirety.

BACKGROUND OF THE INVENTION

The discovery of programmed cell death, known as apoptosis (Greek for "falling to death"), was one of the most exciting and important breakthroughs in biology during the 20th century. Apoptosis is critical for normal embryonic development and adult homeostasis. Impaired apoptosis causes cancer whereas excess apoptosis contributes to major diseases including heart failure and neurodegeneration. Apoptosis is thought to be irreversible after mitochondrial fragmentation and effector caspase activation because, apart from mitochondrial dysfunction, which alone can lead to cell death, initiation of explosive caspase activation causes massive destruction of structural and functional cellular components including the genome. Activated caspases stimulate additional caspases, resulting in the morphological manifestations of apoptosis such as nuclear condensation, cell shrinkage, and membrane blebbing. After mitochondrial release of death effectors including cytochrome c, it is assumed that caspase activation and apoptosis inevitably follow.

An unexpected reversibility of late-stage apoptosis was recently discovered, which is called anastasis (Greek for "rising to life"). The vast majority of primary mouse liver and NIH3T3 human fibroblasts can reverse apoptosis and survive, even after the cells pass through critical checkpoints generally thought to be the point of no return including mitochondrial fragmentation and caspase-3 activation. Simply removing the apoptotic inducers by washing is sufficient to promote reversal of the process, indicating for the first time that anastasis is a mechanism that allows normal cells to arrest at the execution stage and ultimately recover. Notably, the cells that reverse apoptosis acquire genetic alterations and exhibit an increased frequency of colony formation in soft agar and anchorage independent growth. While oncogenic transformation is a negative consequence, the present inventors propose that there may also be multiple beneficial effects of this process. For example, anastasis may have evolved to salvage cells that are difficult to replace, such as mature neurons in the aging brain or adult heart cells. An organism may be better off preserving such cells, even if they are damaged, rather than allowing them to die.

Accordingly, new and innovative approaches are needed to study this newly discovered and fundamental cellular process. Elucidation of the mechanisms governing and executing anastasis could transform scientific understanding and lead to entirely new strategies for the prevention and treatment of degenerative diseases, ischemic diseases, and cancer.

DETAILED DESCRIPTION OF THE INVENTION

Figures 1A, 1B, 1C:
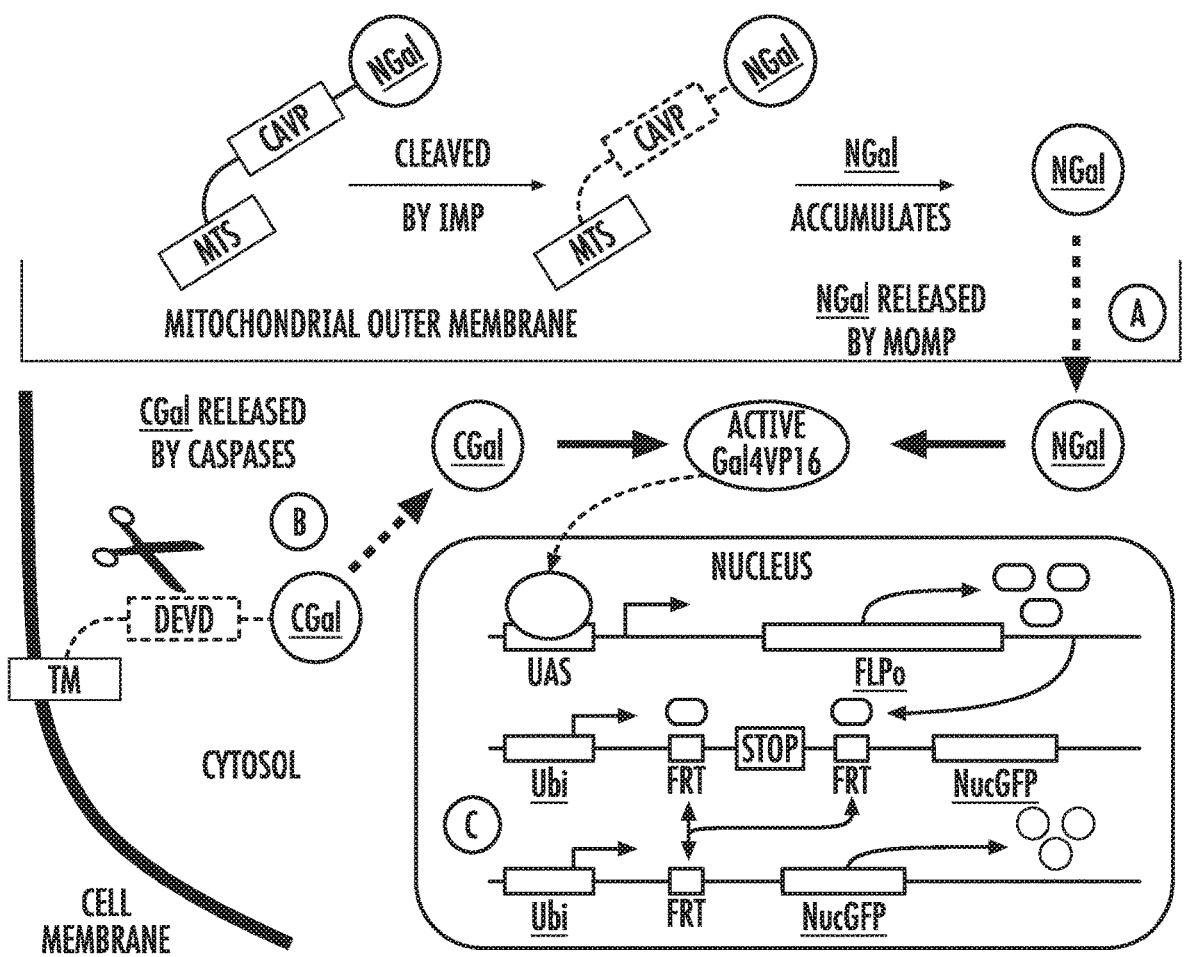
FIG. 1A-B. Design of a Split Gal4-based biosensor to detect concurrent mitochondrial outer membrane permeabilization (MOMP) (FIG. 1A) and caspase-3 activation (FIG. 1B) via a fluorescent protein reporter (FIG. 1C).

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Despite dramatic scientific and technological advances, cancer remains a major and growing public health problem in the United States. Chemotherapy and radiotherapy kill cancer cells by inducing them to die through a cell death process called apoptosis (Greek for "falling to death"). Primary cancers such as childhood acute promyelocytic leukemia and metastatic testicular cancer are often responsive to the therapies and have low recurrence rates. However, most metastatic cancers, including childhood diffuse pontine glioma, lung and pancreatic cancers, typically recur, leading to treatment failure. New treatments such as angiogenesis inhibitors that cut off the blood supply to tumors, and targeted therapies that interfere with the cancer cell division, have been developed. However, these therapies only manage, but do not cure the disease. This results in a suboptimal quality of life for patients and continuous high medical expenses. Therefore, there is an urgent need for novel therapeutic strategies. Currently, cancer research is based on the general assumption that the initiation of cell death (apoptosis) is intrinsically irreversible. However, the present inventors recently discovered that, in fact, many human cancer cells can reverse the cell death process even at late stages and then survive. This recovery phenomenon was named Anastasis (Greek for "rising to life"). Simply removing the cell death-inducing toxin can allow dying cancer cells to recover and then proliferate, indicating that anastasis is a natural phenomenon. Our discovery of anastasis is significant, because it reveals an unexpected tactic that cancer cells can use to escape cancer therapy. Noticeably, most chemotherapy and radiotherapy are delivered episodically to let patients recover from the side effects between successive treatments. However, this also allows cancer cells to recover. Therefore, dying cancer cells that recover by undergoing anastasis during the intervals between cycles of anti-cancer treatments can survive, and then repopulate, leading to cancer recurrence. Importantly, some cells that reversed the dying process acquire new mutations by harboring damaged DNA caused during the cell death process. Therefore, the surviving cancer cells with new DNA mutations can contribute to cancer progression that leads to an increase in drug resistance. The ultimate goal of our research is to harness the discovery of anastasis to develop revolutionary new therapies to fight cancers.

As used herein, the term "polynucleotide" or "nucleic acid" refers to a polymeric form of nucleotides of any length, either ribonucleotides and/or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P—$NH_2$) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support.

The term "promoter" refers to the DNA region, usually upstream of the coding sequence of a gene or operon, which binds RNA polymerase and directs the enzyme to the correct transcriptional start site.

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors," which comprise the attributes of more than one type of vector A "site-specific recombination event" refers to an event catalyzed by a system generally consisting of three elements: a pair of DNA sequences (the site-specific recombination sequences or sites) and a specific enzyme (the site-specific recombinase). The site-specific recombinase catalyzes a recombination reaction only between two site-specific recombination sequences depending on the orientation of the site-specific recombination sequences. Sequences intervening between two site-specific recombination sites will be inverted in the presence of the site-specific recombinase when the site-specific recombination sequences are oriented in opposite directions relative to one another (i.e., inverted repeats). If the site-specific recombination sequences are oriented in the same direction relative to one another (i.e., direct repeats), then any intervening sequences will be deleted upon interaction with the site-specific recombinase. Thus, if the site-specific recombination sequences are present as direct repeats at both ends of vector backbone sequences integrated into a eukaryotic genome, such integration of said sequences can subsequently be removed by interaction of the site-specific recombination sequences with the corresponding site specific recombinase.

A number of different site specific recombinase systems can be used including, but not limited to, the Cre/lox system of bacteriophage P1, the FLP/FRT system of yeast, the Gin recombinase of phage Mu, the Pin recombinase of *E. coli*, the PinB, PinD and PinF from *Shigella*, and the R/RS system of *Zygosaccharomyces rouxii*. Recombinases generally are integrases, resolvases or flippases. Also dual-specific recombinases can be used in conjunction with direct or indirect repeats of two different site-specific recombination sites corresponding to the dual-specific recombinase (WO99/25840). In certain embodiments, site-specific recombinase systems are the bacteriophage P1 Cre/lox and the yeast FLP/FRT and the *Z. rouxii* R/RS systems. In these systems a recombinase (Cre, FLP or R, respectively) interact specifically with its respective site-specific recombination sequence (lox, FRT or RS respectively) to invert or excise the intervening sequences. The site-specific recombination sequences for each of these two systems are relatively short (34 bp for lox and 47 bp for FRT).

To increase the bar for the biosensor to detect and track the recovery of cells after apoptosis rather than non-apoptotic caspase activity, we designed a novel anastasis biosensor to track reversal of apoptosis in cancer cells in vivo. It is understood that this improved biosensor can be used to study anastasis in any cell in vivo.

Figure 2:
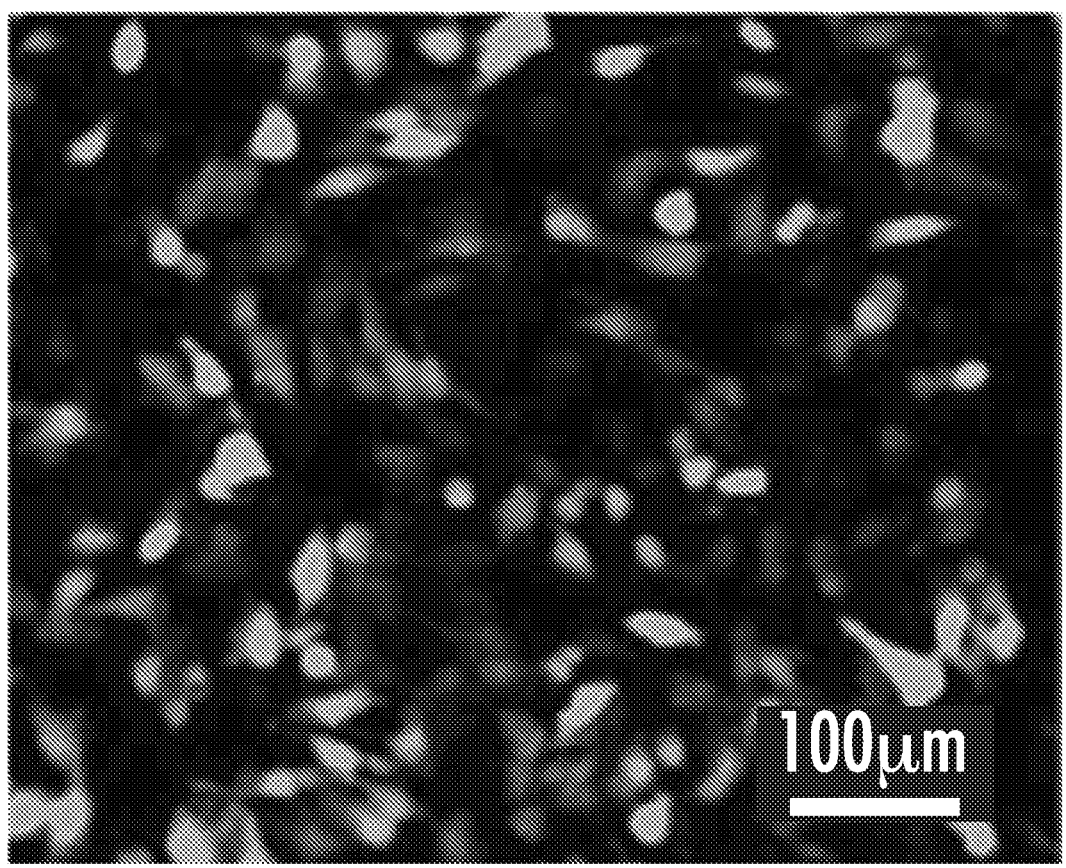
FIG. 2. Concurrent expression of N-Gal and C-Gal triggers Gal4 activity dependent GFP expression in HeLa cells.

In one embodiment, the present invention utilizes of the Split Gal4 system (NGal+CGal=active Gal4-VP16) (Luan et al., 52 NEURON 425-36 (2006)) to create a new generation of biosensor (Split Gal4-based anastasis biosensor), which will label cells only after they have experienced the two most recognized hallmarks at late-stage events of apoptosis: MOMP (mitochondrial outer membrane permeabilization) and caspase-3 activation (FIG. 1). More specifically, the N-terminal fragment of Gal4-VP16 (NGal) is expressed at the mitochondrial intermembrane space by fusing it with the mitochondrial targeting sequence of the MOMP biosensor (Albeck et al., 30 MOL. CELL 11-25 (2008)) (MTSCAVP-NGal), and the C-terminal fragment of Gal4-VP16 (CGal) is tethered to the plasma membrane via a caspase-cleavable peptide and transmembrane domain from the present inventors' previously developed CaspaseTracker (MT-DEVD-CGal) (Tang et al., 100 BR. J. CANCER 118-22 (2009); see also U.S. Patent Application Publication No. 2015/0026834). Therefore, in healthy cells, the NGal and CGal cannot bind together because they are present at two different subcellular locations. However, during apoptosis, NGal is released to the cytosol due to MOMP (FIG. 1A), and CGal is released from plasma membrane due to caspase-3 activation (FIG. 1B). Therefore, NGal and CGal can bind to form Active Gal4-VP16, which then translocates to the nucleus to trigger expression of FLPo to excise the LoxP-flanked stop cassette that separates the Ubi-promotor and GFP, resulting in permanent expression of GFP (FIG. 1C). While Split Gal4 was originally designed for the use in *Drosophila* system, it was found that it also works efficiently in mammalian cells (FIG. 2).

The biosensor is first tested in vitro using HeLa and lung cancer cells, as these cells respond robustly in the anastasis assay (Tang et al., 96 J. VIS. EXP. February 2015, Tang et al., 23 MOL. BIOL. CELL 2240-52 (2012), and Tang et al., 100 BR. J. CANCER 118-22 (2009)). It is expected that the cells that reverse apoptosis after MOMP and caspase-3 activation will display permanent expression of GFP, but not the untreated cells or the treated cells expressing control biosensors, with either non-mitochondrial releasable MTS-CAAA (SEQ ID NO:3)-NGal or non-caspase-3 cleavable MT-DEVA (SEQ ID NO:4)-CGal. After confirming that the anastasis biosensor works in cultured cancer cell lines, anastasis of human lung cancer cells is tested in mice using Small Cell Lung Carcinoma (SCLC xenograft) cancer recurrence mouse model, because (1) robust reversibility of apoptosis was observed in the cultured human lung cancer (SCLC, H446) cells (Tang et al., 96 J. Vis. EXP. February 2015), (2) relapse rate of SCLC in patients is very high even completed response is achieved after initial treatment (>93%) (Davis, A. J. and Tannock, J. F., 1 LANCET ONCOL. 86-93 (2000); Kim, J. J. and Tannock, J. F., 5 NAT. REV. CANCER 516-25 (2005); and Demedts et al., 35 EUR. RESPIR. J. 202-15 (2010), and (3) similar response is observed in clinically relevant human lung cancer (SCLC, H446) recurrence mouse models. To begin, SCLC H446 stable cell line expressing anastasis biosensor are established as described (FIG. 1) (Tang et al., 5 SCI. REP. 9-15 (2015), Tang et al., 96 J. Vis. EXP. February 2015)), engrafted in matrigel (1 million cells in 100 µl), and then injected subcutaneously into the lower flank (under skin) of 6-8 week old athymic nude mice (from Envigo). Palpable tumors with 30-40 mm³ will develop within 4-5-week post-injection. Then, mice with tumor burdens will be treated with hospital grade cancer drugs taxol or irinotecan (50-100 mg/kg) per week by intraperitoneal injection continuously for 3-4 weeks, until a complete response is achieved (tumors no longer palpable/visible to the eye). After the irinotecan treatment, recurrence occurs within 3-4 weeks, with palpable tumors with 10-45 mm³. Tumor tissues are collected to detect GFP expression by fluorescence microscopy. Studies are also conducted to determine if anastasis can occur in normal tissues after cancer therapy leading to secondary tumors in mice, such as acute myeloid leukemia, a common childhood cancer, during recurrence (Chaturvedi et al., 99 J. NATL. CANCER INST. 1634-43 (2007), Travis et al., 97 J. NATL. CANCER INST. 1354-65 (2005), and Smith et al., 21 J. OLIN. ONCOL. 1195-1204 (2003)). For these experiments, anastasis biosensor transgenic mice are generated and tested for GFP expression in second-site tissues such as bone marrow or in the acute myeloid leukemia developed in the cancer drug-treated mice during recurrence. These anastasis biosensor cancer recurrence mouse model will be the essential tools for conducting pre-clinical trials testing the safety and the efficiency of anastasis inhibitor candidates.

In particular embodiments, sensitivity of the biosensor can be increased by increasing the copy number of the caspase cleavage sequence in the linker peptide. In other embodiments, the sensitivity of the biosensor can be adjusted, up or down, by fusing the biosensor with a mutant estrogen ligand-binding domain (ERT2)65 or expressing the biosensor using a tetracycline-responsive promoter66, so that the expression level (sensitivity) of the biosensor will depend on the concentration of tamoxifen or tetracycline, respectively. In further embodiments, the sensitivity of the biosensor can be lowered by using other DEVD-containing linker peptides that are less cleavable then the PARP domain-based linker (Poreba et al., 5 COLD SPRING HARB. PERSPECT. BIOL. A008680 (2013), Takemoto et al., 160 J. CELL BIOL. 235-43 (2003), and Talanian et al., 272 J. BIOL. CHEM. 9677-82 (1997).

Utilizing the split transcription factor/recombinase/intein approach, the biosensors will label cells only after they have experienced the two most recognized hallmarks at late-stage events of apoptosis: MOMP (mitochondrial outer membrane permeabilization) and caspase-3 activation. Examples of the split approach include Split Gal4 (Refined spatial manipulation of neuronal function by combinatorial restriction of transgene expression, Neuron. 2006 52(3) 425-36, Luan H, Peabody N C, Vinson C R, White B H), Split Q (Controlling gene expression with the Q repressible binary expression system in *Caenorhabditis elegans*, Nat Methods. 2012 9(4) 391-5, Wei X, Potter C J, Luo L, Shen K), Split Cre (Split-CreERT2: temporal control of DNA recombination mediated by split-Cre protein fragment complementation, PLoS One. 2009 Dec. 16; 4(12):e8354, Hirrlinger J, Requardt R P, Winkler U, Wilhelm F, Schulze C, Hirrlinger P G), Split FLPase (Reconstruction of Split-recombinase FLP and Its Recombination Activation in Transgenic Tobacco; Sequential gene targeting to make chimeric tumor models with de novo chromosomal abnormalities, Cancer Res. 2014 74(5) 1588-97, Chambers J S, Tanaka T, Brend T, Ali H, Geisler N J, Khazin L, Cigudosa J C, Dear T N, MacLennan K, Rabbitts T H), and Split Intein (Intersectional Cre driver lines generated using split-intein mediated split-Cre reconstitution, Sci Rep. 2012 2 497, Wang P, Chen T, Sakurai K, Han B X, He Z, Feng G, Wang F.). In a further embodiment, the reverse tetracycline transactivator (rtTA) is used, specifically, split rtTA (DNA binding domain and the VP16 domain).

Accordingly, in one embodiment, the present invention provides an anastasis biosensor comprising (a) a first transcription factor complex comprising either the N-terminal or C-terminal fragment of the Gal4 transcription factor linked to a transmembrane domain via an enzyme cleavable linker; (b) a second transcription factor complex comprising either the N-terminal or C-terminal fragment of the Gal4 transcription factor linked to a mitochondrial targeting sequence (MTS) via an enzyme cleavable linker, wherein the N-terminal fragment of the Gal4 transcription factor is used if the first transcription factor complex of element (a) comprises the C-terminal fragment of the Gal4 transcription factor or wherein the C-terminal fragment of the Gal4 transcription factor is used if the first transcription factor complex of element (a) comprises the N-terminal fragment of the Gal4 transcription factor; and (c) a reporter system comprising (1) a first nucleic acid encoding flippase operably linked to the upstream activating sequence that binds Gal4; and (2) a second nucleic acid comprising an FRT-flanked stop codon cassette separating a constitutive promoter and a fluorescent protein open reading frame.

In certain embodiments, the enzyme cleavable linker of element (a) is cleaved by an enzyme specifically expressed during apoptosis. In a specific embodiment, the enzyme of element (a) is a caspase. In other embodiments, the enzyme of element (b) is an inner membrane protease (IMP). The enzyme of element (b) can be any protease expressed inside mitochondria. In particular embodiments, the fluorescent protein comprises green fluorescent protein, red fluorescent protein, or yellow fluorescent protein. The present invention also provides a transgenic mammal comprising a biosensor described herein.

In another embodiment, a biosensor for studying anastasis comprises (a) a caspase-activatable transcription factor complex comprising either the N-terminal or C-terminal fragment of the split Gal4 transcription factor that is linked to a transmembrane domain via a caspase-cleavable linker; (b) an IMP-activatable transcription factor complex comprising either the N-terminal or C-terminal fragment of the split Gal4 transcription factor linked to a MTS via a caspase-cleavable linker; and (c) a reporter system comprising a (1) first nucleic acid encoding flippase operably linked to the upstream activating sequence that binds Gal4; (2) a second nucleic acid comprising an FRT-flanked stop cassette separating a constitutive promoter and a fluorescent protein open reading frame.

In a specific embodiment, the caspase-cleavable linker comprises the amino acid sequence DEVD (SEQ ID NO:1). Alternatively, the linker can comprise the amino acid sequence of SEQ ID NO:5. In another embodiment, the IMP-cleavable linker comprises the amino acid sequence CAVP (SEQ ID NO:2). In certain embodiments, the constitutive promoter is the ubiquitin promoter. The MTS can be the N-terminal end of SMAC (SEQ ID NO:6-7). In a specific embodiment, a biosensor of the present invention comprises the Mito-CAVP (SEQ ID NO:7) and the N-terminal end of rtTA. The C-terminal end of rtTA can be used with the transmembrane domain. In particular embodiments, the biosensor of the present invention can also comprise a transient reporter in the nucleus. For example, the dual biosensor of the CaspaseTracker (Tang et al., 5 Sci. Rep. 9015 (2015) (see FIG. 1 of Tang et al.)) can be used to signal ongoing or transient, as well as permanent reporter expression.

The present invention also provides a biosensor comprising (a) a caspase-activatable transcription factor complex comprising either the N-terminal or C-terminal fragment of the split Gal4 transcription factor linked to a transmembrane domain via a caspase-cleavable linker; (b) an IMP-activatable transcription factor complex comprising either the N-terminal or C-terminal fragment of the split Gal4 transcription factor linked to a MTS via an IMP-cleavable linker; and (c) the G-TRACE reporter system.

In yet another embodiment, the present invention provides a biosensor system comprising (a) a caspase-activatable recombinase complex comprising one half of the split Cre recombinase protein linked to a transmembrane domain via a caspase-cleavable linker; (b) an IMP-activatable recombinase complex comprising the other half of the split Cre recombinase protein linked to a MTS via an IMP-cleavable linkers; and (c) a nucleic acid comprising a LoxP-flanked stop codon cassette separating a constitutive promoter and a fluorescent protein open reading frame.

In an alternative embodiment, a biosensor system comprises (a) a split site-specific recombinase tethered to the plasma membrane of a test cell, wherein the split recombinase is linked to a transmembrane domain via an enzyme cleavable linker; (b) a split site-specific recombinase comprising the other half of the split recombinase of element (a) expressed in the mitochondria of the test cell, wherein the split recombinase is linked to a MTS via an enzyme cleavable linker; and (c) a nucleic acid encoding a reporter gene operably linked to a promoter, wherein the recognition target sequence of the recombinase flanks a stop codon cassette located between the reporter gene and the promoter.

In a specific embodiment, the site-specific recombinase is flippase and the recognition target sequence is FRT. In particular embodiments, the reporter gene encodes a fluorescent protein. In a certain embodiments, the promoter is a constitutive promoter. In specific embodiments, the enzyme of element (a) is caspase. In other embodiments, the enzyme of element (b) is IMP.

The present invention also provides a biosensor comprising (a) a split transcription factor complex comprising one half of a split transcription factor linked to a transmembrane domain via an enzyme cleavable linker; (b) a split transcription factor comprising the other half of the split transcription factor linked to a MTS via an enzyme-cleavable linker; and (c) a reporter system comprising (1) a first nucleic acid encoding a site specific recombinase operably linked to the site specific sequence for the transcription factor; and (2) a second nucleic acid comprising a stop codon cassette flanked by site specific recombination sequences, wherein the split transcription factor is Gal 4 or split Q. In other embodiments, the recombinase is Cre or FLP. The fluorescent protein can comprise green fluorescent protein, red fluorescent protein, or yellow fluorescent protein. The present invention also provides kits comprising one or more of the constructs described herein, as well as the necessary reagents, controls and instructions.

The biosensors of the present invention can be used for drug screening. In certain embodiments, the biosensors can be expressed in organoids from a patient. Drugs that kill cancer cells without anastasis can be screened. If the biosensor indicates that anastasis is occurring or likely to occur, then other drugs can be used or an anastasis inhibitor could also be used to prevent cancer recurrence during and after drug treatment. In alternative embodiments, the screening can take place using patient-derived xenograft mice. See, e.g., Pauli et al., 7(5) Cancer Discov. 462-77 (2017).

We claim:

1. An anastasis biosensor comprising:
   (a) a first transcription factor complex comprising either the N-terminal or C-terminal fragment of the Gal4 transcription factor linked to a transmembrane domain via an enzyme cleavable linker;
   (b) a second transcription factor complex comprising either the N-terminal or C-terminal fragment of the Gal4 transcription factor linked to a mitochondrial targeting sequence (MTS) via an enzyme cleavable linker, wherein the N-terminal fragment of the Gal4 transcription factor is used if the first transcription factor complex of element (a) comprises the C-terminal fragment of the Gal4 transcription factor or wherein the C-terminal fragment of the Gal4 transcription factor is used if the first transcription factor complex of element (a) comprises the N-terminal fragment of the Gal4 transcription factor; and
   (c) a reporter system comprising (1) a first nucleic acid encoding flippase operably linked to the upstream activating sequence that binds Gal4; and (2) a second nucleic acid comprising an FRT-flanked stop codon cassette separating a constitutive promoter and a fluorescent protein open reading frame.

2. The anastasis biosensor of claim 1, wherein the enzyme cleavable linker of element (a) is cleaved by an enzyme specifically expressed during apoptosis.

3. The anastasis biosensor of claim 1, wherein the enzyme of element (a) is a caspase.

4. The anastasis biosensor of claim 1, wherein the enzyme of element (b) is an inner membrane protease (IMP).

5. The anastasis biosensor of claim 1, wherein the fluorescent protein comprises green fluorescent protein, red fluorescent protein, or yellow fluorescent protein.

6. A transgenic mammal comprising the biosensor of claim 1.

7. A biosensor comprising:
   (a) a caspase-activatable transcription factor complex comprising either the N-terminal or C-terminal fragment of the split Gal4 transcription factor that is linked to a transmembrane domain via a caspase-cleavable linker;
   (b) an IMP-activatable transcription factor complex comprising either the N-terminal or C-terminal fragment of the split Gal4 transcription factor linked to a MTS via an IMP-cleavable linker, wherein the N-terminal fragment of the Gal4 transcription factor is used if the caspase-activatable transcription factor complex of element (a) comprises the C-terminal fragment of the Gal4 transcription factor or wherein the C-terminal fragment of the Gal4 transcription factor is used if the caspase-activatable transcription factor complex of element (a) comprises the N-terminal fragment of the Gal4 transcription factor; and
   (c) a reporter system comprising a (1) first nucleic acid encoding flippase operably linked to the upstream activating sequence that binds Gal4; (2) a second nucleic acid comprising an FRT-flanked stop cassette separating a constitutive promoter and a fluorescent protein open reading frame.

8. The biosensor of claim 7, wherein the caspase-cleavable linker comprises the amino acid sequence DEVD (SEQ ID NO:1).

9. The biosensor of claim 7, wherein the IMP-cleavable linker comprises the amino acid sequence CAVP (SEQ ID NO:2).

10. The biosensor of claim 7, wherein the constitutive promoter is the ubiquitin promoter.

11. A biosensor comprising:
    (a) a caspase-activatable transcription factor complex comprising either the N-terminal or C-terminal fragment of the split Gal4 transcription factor linked to a transmembrane domain via a caspase-cleavable linker;
    (b) an IMP-activatable transcription factor complex comprising either the N-terminal or C-terminal fragment of the split Gal4 transcription factor linked to a MTS via an IMP-cleavable linker, wherein the N-terminal fragment of the Gal4 transcription factor is used if the caspase-activatable transcription factor complex of element (a) comprises the C-terminal fragment of the Gal4 transcription factor or wherein the C-terminal fragment of the Gal4 transcription factor is used if the caspase-activatable transcription factor complex of element (a) comprises the N-terminal fragment of the Gal4 transcription factor; and (c) the G-TRACE reporter system.

12. A biosensor system comprising:
(a) a caspase-activatable recombinase complex comprising one half of the split Cre recombinase protein linked to a transmembrane domain via a caspase-cleavable linker;
(b) an IMP-activatable recombinase complex comprising the other half of the split Cre recombinase protein linked to a MTS via an IMP-cleavable linkers; and
(c) a nucleic acid comprising a LoxP-flanked stop codon cassette separating a constitutive promoter and a fluorescent protein open reading frame.

13. A biosensor system comprising:
(a) a split site-specific recombinase comprising one half of the split site-specific recombinase tethered to the plasma membrane of a test cell, wherein the one half of the split recombinase is linked to a transmembrane domain via an enzyme cleavable linker;
(b) a split site-specific recombinase comprising the other half of the split recombinase of element (a) expressed in the mitochondria of the test cell, wherein the other half of the split recombinase is linked to a MTS via an enzyme cleavable linker; and
(c) a nucleic acid encoding a reporter gene operably linked to a promoter, wherein the recognition target sequence of the recombinase flanks a stop codon cassette located between the reporter gene and the promoter.

14. The biosensor system of claim 13, wherein the site-specific recombinase is flippase and the recognition target sequence is FRT.

15. The biosensor system of claim 13, wherein the reporter gene encodes a fluorescent protein.

16. The biosensor system of claim 13, wherein the promoter is a constitutive promoter.

17. The biosensor system of claim 13, wherein the enzyme of element (a) is caspase.

18. The biosensor system of claim 13, wherein the enzyme of element (b) is IMP.

19. A biosensor comprising:
(a) a split transcription factor complex comprising one half of a split transcription factor linked to a transmembrane domain via an enzyme cleavable linker; and
(b) a split transcription factor comprising the other half of the split transcription factor linked to a MTS via an enzyme-cleavable linker; and
(c) a reporter system comprising (1) a first nucleic acid encoding a site specific recombinase operably linked to the site specific sequence for the transcription factor; and (2) a second nucleic acid comprising a stop codon cassette flanked by site specific recombination sequences, wherein the stop codon cassette and flanking sequences separate a constitutive promoter and a fluorescent protein open reading frame.

20. The biosensor of claim 19, wherein the enzyme cleavable linker of element (a) is cleaved by an enzyme specifically expressed during apoptosis.

21. The biosensor of claim 20, wherein the enzyme is caspase.

22. The biosensor of claim 19, wherein the enzyme of element (b) is an inner membrane protease (IMP).

23. The biosensor of claim 19, wherein the split transcription factor is Gal 4 or split Q.

24. The biosensor of claim 19, wherein the recombinase is Cre or FLP.

25. The biosensor of claim 19, wherein the fluorescent protein comprises green fluorescent protein, red fluorescent protein, or yellow fluorescent protein.

* * * * *